(12) United States Patent
Digiovanna et al.

(10) Patent No.: US 9,050,200 B2
(45) Date of Patent: Jun. 9, 2015

(54) SYSTEM AND METHOD FOR BRAIN MACHINE INTERFACE (BMI) CONTROL USING REINFORCEMENT LEARNING

(75) Inventors: John F. Digiovanna, Zurich (CH); Babak Mahmoudi, Gainesville, FL (US); Jeremiah D. Mitzelfelt, Gainesville, FL (US); Justin C. Sanchez, Gainesville, FL (US); Jose C. Principe, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 973 days.

(21) Appl. No.: 12/598,217

(22) PCT Filed: Apr. 25, 2008

(86) PCT No.: PCT/US2008/061549
§ 371 (c)(1),
(2), (4) Date: Oct. 30, 2009

(87) PCT Pub. No.: WO2008/137346
PCT Pub. Date: Nov. 13, 2008

(65) Prior Publication Data
US 2010/0137734 A1 Jun. 3, 2010

Related U.S. Application Data

(60) Provisional application No. 60/915,469, filed on May 2, 2007.

(51) Int. Cl.
*A61B 5/04* (2006.01)
*A61F 2/68* (2006.01)
(Continued)

(52) U.S. Cl.
CPC .............. *A61F 2/68* (2013.01); *G05B 13/0265* (2013.01); *A61B 5/0482* (2013.01); *A61F 2/72* (2013.01); *G06F 3/015* (2013.01); *G06N 3/08* (2013.01)

(58) Field of Classification Search
CPC ..................... G06F 3/015; G06N 3/88; A61B 2018/00446; A61B 5/04888; A61B 5/7267; A61B 5/0476; A61F 2/72; G05B 13/0265; G05B 13/027; G05B 13/0285
USPC ....... 600/544–546; 706/23; 704/232; 607/61; 623/25
See application file for complete search history.

(56) References Cited

U.S. PATENT DOCUMENTS 6,169,981 B1  1/2001  Werbos
6,171,239 B1 *  1/2001  Humphrey .................... 600/372
(Continued)

FOREIGN PATENT DOCUMENTS

WO  2000009008 A  2/2000
WO  2003037231 A  5/2003

OTHER PUBLICATIONS

Wei Ying-zi; Zhao Ming-yang. "Effective strategies for complex skill real-time learning using reinforcement learning," Oct. 8-13, 2003, 2003 IEEE International Conference on Robotics, Intelligent Systems and Signal Processing, 2003. Proceedings. vol. 1, pp. 388-392.*
(Continued)

*Primary Examiner* — Navin Natnithithadha
*Assistant Examiner* — Eric Messersmith
(74) *Attorney, Agent, or Firm* — Thomas | Horstemeyer, LLP.

(57) ABSTRACT

A Brain Machine Interface (BMI) agent (110) is provided, that when operatively coupled to a subject during a mental task by the subject to control a prosthetic device (130), monitors one or more states (125) of neural activity of the subject, receives feedback associated with a behavior of the prosthetic device responsive to the control, learns a functional mapping between the mental task and the behavior in view of the feedback, and applies at least one control action (115) to the prosthetic device in accordance with the learning to control the prosthetic device for a targeted behavior.

28 Claims, 4 Drawing Sheets

(51) Int. Cl.

| | |
|---|---|
| *G05B 13/02* | (2006.01) |
| *A61B 5/0482* | (2006.01) |
| *A61F 2/72* | (2006.01) |
| *G06F 3/01* | (2006.01) |
| *G06N 3/08* | (2006.01) |

(56) References Cited

U.S. PATENT DOCUMENTS

| | | | | |
|---|---|---|---|---|
| 6,581,048 | B1* | 6/2003 | Werbos | 706/23 |
| 7,058,445 | B2* | 6/2006 | Kemere et al. | 600/545 |
| 7,403,904 | B2* | 7/2008 | Abe et al. | 705/7.29 |
| 7,901,368 | B2* | 3/2011 | Flaherty et al. | 601/5 |
| 2003/0074338 | A1* | 4/2003 | Young et al. | 706/15 |
| 2003/0093129 | A1* | 5/2003 | Nicolelis et al. | 607/45 |
| 2004/0267320 | A1* | 12/2004 | Taylor et al. | 607/2 |
| 2005/0228515 | A1* | 10/2005 | Musallam et al. | 700/83 |
| 2006/0217816 | A1* | 9/2006 | Pesaran et al. | 623/25 |
| 2008/0249844 | A1* | 10/2008 | Abe et al. | 705/10 |

OTHER PUBLICATIONS

Thrasher et al. "Self Adaptive Neuro-Fuzzy Control of Neural Prostheses Using Reinforcement Learning" Engineering in Medicine and Biology Society, 1996. Bridging Disciplines for Biomedicine. Proceedings of the 18th Annual International Conference of the IEEE. Oct. 31-Nov. 3, 1996. vol. 1, pp. 451-452.*

Martin, P. and Millan, J.D.R. "A Modular Reinforcement-Based Neural Controller for a Three-Link Manipulator" Intelligent Robots and Systems, 1997. IROS '97., Proceedings of the 1997 IEEE/RSJ International Conference on. Sep. 7-11, 1997. vol. 2, pp. 785-792.*

Rotermund et al. "Towards on-line adaptation of neuro-prostheses with neuronal evaluation signals" Biol Cybern. 2006. 95:243-257.*

Taylor et al. "Direct Cortical Control of 3D Neuroprosthetic Devices" Science. Jun. 7, 2002. vol. 296 No. 5574 pp. 1829-1832.*

Serruya et al. "Instant neural control of a movement signal"Mar. 14, 2002. Nature. 416(6877):141-2.*

Morris et al. "Midbrain dopamine neurons encode decisions for future action" Aug. 2006. Nature Neuroscience. 9(8):1057-63.*

Glorennec, P.Y. "Fuzzy Q-learning and dynamical fuzzy Q-learning" Fuzzy Systems, 1994. IEEE World Congress on Computational Intelligence., Proceedings of the Third IEEE Conference on. Jun. 26-29, 1994. vol. 1. 474-479.*

Wolpaw et al. "Brain-computer interfaces for communication and control" 2002 Clinical Neurophysiology vol. 113 pp. 767-791.*

De Vries and Principe, "The Gamma Model—A New Neural Model for Temporal Processing," 1992, Neural Networks, vol. 5, Issue 4, pp. 565-576.*

Hsu, et al. "Context analysis by the gamma neural network" 1996. IEEE International Conference on Neural Networks, vol. 2, 682-687.*

Wang, F. (1999). Adaptive fuzzy network with application to neural prosthetic control: A computer simulation study. (Order No. MQ40121, University of Alberta (Canada)). ProQuest Dissertations and Theses, , 193-193 p. Retrieved from http://search.proquest.com/docview/304547506?accountid=14753.*

The International Search Report on Patentability dated Nov. 12, 2009.

The International Search Report and Written Opinion dated Nov. 18, 2008.

Voltage Comparator Information and Circuits, http://home.cogeco.ca/~rpaisley4/Comparators.html, Jun. 23, 2005, pp. 1-28.

Chen, et al., "Biphasic Pulse Signal Coding," Feb. 2005.

* cited by examiner

| Data | Dimension | Max | Mean | Standard Dev. |
|---|---|---|---|---|
| Neural | 2 | 81.3 % | 61.9 % | 10 % |
| Neural | 3 | 81.3 % | 68.1 % | 10.8% |
| Neural | 3* | 75 % | 50 % | 15.6 % |
| Surrogate | 2 | 43.8 % | 23.1 % | 11 % |
| Surrogate | 3 | 43.8 % | 34.3 % | 7.3 % |
| Surrogate | 3* | 43.8 % | 31.8 % | 8.56 % |

SYSTEM AND METHOD FOR BRAIN MACHINE INTERFACE (BMI) CONTROL USING REINFORCEMENT LEARNING

STATEMENT AS TO FEDERALLY SPONSORED RESEARCH

The invention was made with U.S. government support under grant number CNS-0540304 awarded by the National Science Foundation. The U.S. government has certain rights in the invention.

CROSS REFERENCE TO RELATED APPLICATION

This application claims priority to, and the benefit of, the PCT application entitled "SYSTEM AND METHOD FOR BRAIN MACHINE INTERFACE (BMI) CONTROL USING REINFORCEMENT LEARNING," having serial number PCT/US2008/061549, filed on Apr. 25, 2008, which claims priority to, and the benefit of, U.S. provisional application having Ser. No. 60/915,469 and filed on May 2, 2007.

FIELD OF THE INVENTION

The present invention relates to the field of biomedical signal processing, and more particularly, to a system and method for Brain Machine Interface (BMI) control using reinforcement learning.

BACKGROUND

The number of patients suffering from motor neuropathies increases every year. Traumatic spinal cord injury, stroke, neuro-degenerative diseases, and amputations are a few of the conditions that lead to motor control deficits. Patients with such conditions can benefit from prosthetic technologies to replace missing or nonfunctional limbs, or technologies to restore muscle control and function.

Traditionally, Brain Machine Interface (BMI) research has attempted to find functional relationships between neuronal activity and goal directed movements using supervised learning (SL) techniques in an input-output modeling framework. This approach fundamentally requires knowledge of the inputs (neural activity) and a desired response (behavioral kinematics). However, the requirement of behavioral kinematics (patient movements) is a fundamental limitation when applying BMI technology in the clinical setting with patients that may be otherwise unable to provide a desired response (e.g. physical movements) to train the BMI system.

Accordingly a need exists for a system and method for BMI control that uses a semi-supervised learning paradigm, such as reinforcement learning. This control system allows the patient to learn to control the BMI. Additionally, the BMI can adapt to the patient's behavior.

SUMMARY

One embodiment is a Brain Machine Interface (BMI) agent, that when operatively coupled to a subject during a mental task by the subject to control a prosthetic device, monitors one or more states of neural activity of the subject, receives feedback (e.g. reward) associated with a behavior of the prosthetic device responsive to the control, learns a functional mapping between the mental task and the behavior in view of the feedback, and applies control actions to the prosthetic device in accordance with the learned functional mapping to maneuver the prosthetic device for a targeted behavior.

The BMI agent can include a detection system to detect and collect neurophysiological signals comprising control action potentials of single or ensembles of neurons in a neural structure, an analysis system to determine the states of the neurophysiological signals and assess one or more rewards associated with the behavior of the prosthetic device, and a controller that applies the control action to the prosthetic device to adjust the behavior of the prosthetic device in accordance with the functional mapping. The analysis system can include a neural network that generates the functional mapping between the states and the control actions of the prosthetic device using reinforcement learning (RL) to learn an association between the states and the control actions. At the same time, the user is learning the relationship between their own brain activity and BMI control. This interaction of two learning systems is called 'co-adaptation'.

In one arrangement, the neural network comprises a Gamma structure front-end with time varying Gamma weight kernels, and a greedy policy back-end to evaluate exploratory control actions of the prosthetic device that produce a targeted behavior. In one configuration, the neural network can learn from sequences of state-control action pairs using Watkins Q($\lambda$) reinforcement learning (RL) or any other RL learning technique (e.g. SARSA, Q learning, TD-learning, etc). The neural network can use the one or more rewards to update (learn) the functional mapping, wherein the reward is provided responsive to a prior controlled movement of the prosthetic device, and the state is a spatio-temporal neural firing pattern. It should be understood that the Gamma front-end time delay and the greedy policy back-end are but one example used in an embodiment and that any number of different front-ends or back-end policies can be used within contemplation of the claimed embodiments herein.

The detection system can include an array having a plurality of electrodes forming a multi-site array to record neural activities, and a spike sorter to extract neural firing features from the neural activities and distinguish between neurons generating the neural activities. The analysis system can evaluate the detected and collected neurophysiological signals and perform a real-time control action of neuron firing features, and from the neuron firing features determine the state-action pairs associated with the one or more rewards.

Another embodiment is a neural prosthetic system that can include a micro-electrode array electro-chemically coupled to a neural structure of a subject to capture neural activity in the neural structure, a prosthetic device that performs one or more behaviors for the subject in accordance with the neural activity, and a Brain Machine Interface (BMI) agent operatively coupled to the micro-electrode array and the prosthetic device. The BMI agent can monitor one or more states of the neural activity, receive feedback associated (including extracting reward signals from the brain) with a behavior of the prosthetic device, learn a functional mapping between the neural activity and the one or more behaviors in view of the feedback, and apply an control action to the prosthetic device in accordance with the learning to control the prosthetic device for a targeted behavior. In one arrangement, the prosthetic device is a robotic appendage, and the BMI agent controls the robotic appendage in a three-dimensional coordinate space in accordance with the one or more states of the neural activity. The target behavior can be a positioning of the robotic appendage endpoint along at least one point of a three-dimensional trajectory in the three-dimensional coordinate space.

The BMI agent can include a detection system communicatively coupled to the micro-electrode array to determine neural firing rates from the neural activity, an analysis system communicatively coupled to the detection system to determine the states from the neural firing rates, and a controller to apply an control action to the prosthetic device to adjust the behavior of the prosthetic device in accordance with the functional mapping. The analysis system can include a neural network that generates the functional mapping between the states and the control action of the prosthetic device using reinforcement learning (RL) to learn (while co-adapting with the patient) an association between the states and the control action. The neural network can include a Gamma structure front-end with arbitrary time varying Gamma weight kernels, and a Greedy policy back-end to evaluate exploratory control actions of the prosthetic device that produce a targeted behavior. The neural structure can be within the motor-cortex, sensory cortex, parietal cortex, cerebellum, red nuclei, basil ganglia, limbic system, hippocampus, entorhinal cortex, CA1, CA2, CA3, dentate, and hippocampal commissure. The BMI agent can be implemented in a Digital Signal Processor, an Application Specific Integrated Circuit (ASIC), a programmable memory, a Random Access Memory (RAM), a Read Only Memory (ROM), micro-controller, or any other computer readable or programmable storage medium.

Yet another embodiment is a method for Brain Machine Interface (BMI) control. The method can include capturing neural signals in a neural structure of a subject during a mental task by the subject to control a prosthetic device, receiving feedback associated with a prior behavior of the prosthetic device responsive to the control, learning a functional mapping between the mental related task and the behavior in view of the feedback; and applying an control action to the prosthetic device in accordance with the learning to control the prosthetic device for a targeted behavior.

A neural network can receive as input the neural signals and one or more rewards associated with the behavior of the prosthetic device, and adapt one or more weights of the neural network using a reinforcement learning policy that associates one or more states of the neural activity with a control action for the prosthetic device. The method can include pre-processing the neural signals with a non-linear gamma time-delay kernel prior to input to the neural network, and implementing a $\epsilon$-greedy policy (or other policy) back-end to evaluate exploratory control actions of the prosthetic device that produce a targeted behavior.

In one arrangement, the neural network can control an endpoint position of a robotic appendage of the prosthetic device operating in a three-dimensional space to reach a set of targets. The one or more rewards identify positions of the robotic appendage in the three-dimensional space, wherein a positive reward is generated when the robotic appendage reaches a target location. The neural network can be trained using semi-supervised learning with inputs corresponding to the one or more input states composed of the neural signals and outputs corresponding to the positions of the robotic appendage. The neural network can learn from sequences of state-control action pairs that generate movement trajectories of the robotic appendage.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Broadly stated, embodiments are directed to a brain machine interface (BMI) system that can translate neural activity into goal directed behaviors. The BMI system allows for the control of computers or prosthetic devices without requiring knowledge of the physical actuation of the behaviors. In particular, the BMI system implements reinforcement learning (RL), instead of a supervised learning (SL), to find a functional mapping between neural activity and behavior which completes goal-directed tasks. The RL framework provides a mechanism of learning that is similar to operant conditioning of biological organisms because the learner is not told what control actions to take, but must discover which control actions yield the most reward through 'trial and error' learning. The BMI system through RL enables the learners (both the BMI agent and BMI user) to interact with their environment to maximize rewards.

In the foregoing, a semi-supervised BMI control architecture that uses reinforcement learning (RL) is provided to find the neural state to motor mapping in goal-directed tasks though co-adaptation. The formulation of the RL architecture is presented in the context of a BMI system (RLBMI) that controls a prosthetic limb using a robot. Experimental results and simulations can be provided for controlling the endpoint position of the robot operating in a three-dimensional workspace to reach a set of targets. Embodiments of the BMI system are suitable for use with paralyzed patients (or patients with other motor neuropathies) that are unable to generate the movement trajectories necessary for BMI training.

Figure 1:
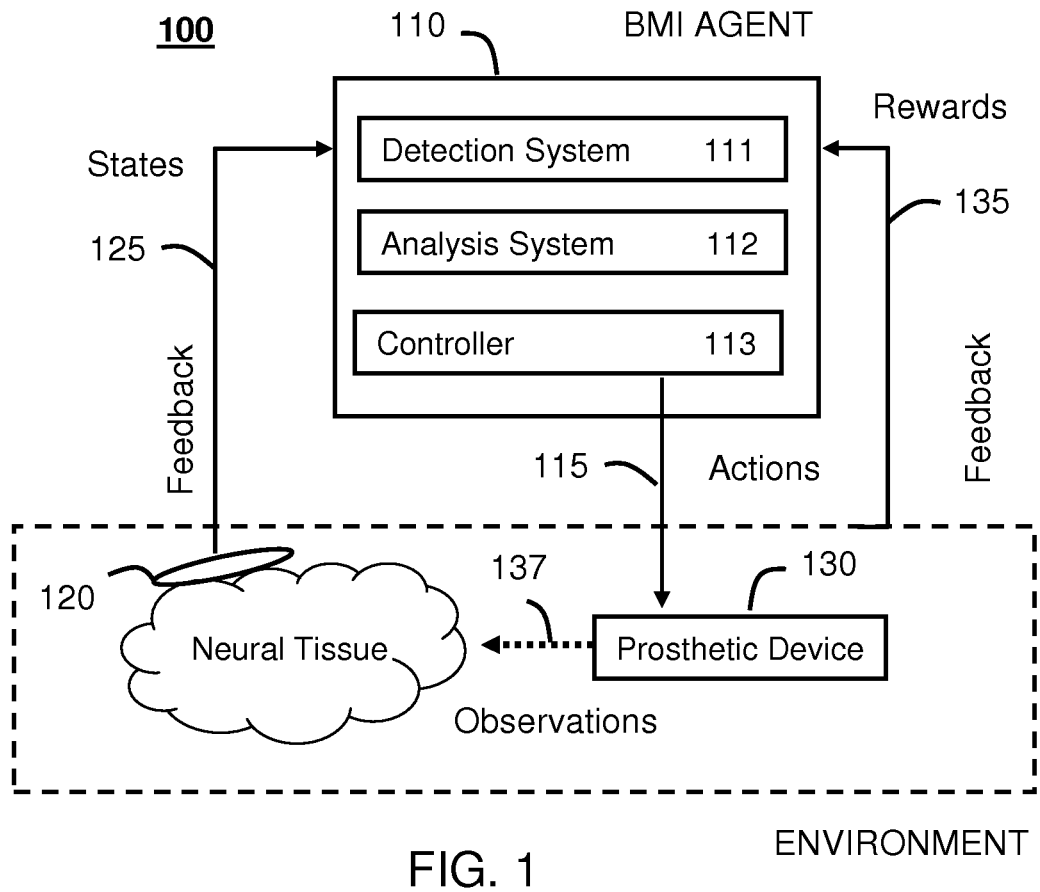
FIG. 1 depicts an exemplary embodiment of a Brain Machine Interface (BMI) system.

Referring to FIG. 1, a BMI system 100 is shown. The BMI system 100 can include a micro-electrode array 120 electrochemically coupled to a neural structure of a subject to capture neural activity in the neural structure, a prosthetic device 130 that performs one or more behaviors for the subject in accordance with the neural activity, and a Brain Machine Interface (BMI) agent 110 operatively coupled to the micro-electrode array 120 and the prosthetic device 130 that monitors one or more states 125 of the neural activity, receives feedback associated with a behavior of the prosthetic device, learns a functional mapping between the neural activity and the one or more behaviors in view of the feedback, and applies an control action 115 to the prosthetic device in accordance with the learning to control the prosthetic device for a targeted behavior.

The BMI agent 110 can include a detection system 111 communicatively coupled to the micro-electrode array 120 to determine neural firing rates from the neural activity, an analysis system 112 communicatively coupled to the detection system 111 to determine the states from the neural firing rates and assess one or more rewards 137 associated with a behavior of the prosthetic device 130, and a controller 113 to apply one or more control actions 115 to the prosthetic device 130 to adjust the behavior of the prosthetic device 130 in accordance with the learned state-action value function.

The detection system 111 can include an array of a plurality of electrodes forming a multi-site array 120 to record neural activities, and a spike sorter to extract neural firing features from the neural activities and distinguish between neurons generating the neural activities. The analysis system can evaluate the detected and collected neurophysiological signals and perform a real-time control action of neuron firing features, and from the neuron firing features determine the states associated with the one or more rewards 137. In one arrangement, the control action 115 is a relative movement of a robotic appendage of the prosthetic device in a three-dimensional coordinate space, and the target behavior is a positioning of the robotic appendage along at least one point of a three-dimensional trajectory in the three-dimensional coordinate space.

In one embodiment, the BMI system 100 can be used to help a patient control a prosthetic device, such as a robotic appendage of a prosthetic limb. The micro-electrode 120 can be placed on a neural structure (e.g. brain tissue) of the patient to record neural signals which are sent to the BMI agent 110. The BMI agent 110 can send control actions to the robot appendage to control a movement of the prosthetic limb in accordance with the neural signals. The control actions can be a relative movement of the prosthetic limb in a three-dimensional coordinate space (e.g. up, down, left, right). The patient can observe the prosthetic limb movement and attempt to direct the prosthetic limb to perform a target behavior, such as moving to a specific location. The BMI agent 110 can generate a functional mapping between one or more states of the neural signals and the one or more control actions using RL techniques.

The BMI agent 110 can be considered a model for conducting a task (through RL or other methods) to achieve a goal. The states 125 of the environment and rewards 137 gained teach the BMI agent 110 an optimal selection "policy" or state-action value. The 'policy' interprets the state-action value to select control actions. The BMI agent 110 can assess the rewards 137 during the controlled movement to update the functional mapping. A positive reward 137 is associated with a targeted behavior of the prosthetic limb, such as a controlled positioning. The rewards 137 are application and context specific; can be established by the BMI designer (manually or through a detection system). As an example, the rewards 137 can be established for moving the prosthetic limb along a motion trajectory in a controlled manner. Note, the reward can also be brain extracted rewards where it is likely that a detection system can be used to convert firing rates to expected rewards.

In a BMI experimental paradigm, wherein an animal test subject (e.g. rat) is used, the BMI designer has access to the environment, the control actions, the rewards, and also the real animal brain signals, i.e. one can observe the spatio-temporal activation of brain states (indirectly related to the environment) as the animal seeks a goal or the completion of a task. Relative to the 'agent' (i.e. BMI agent 110), neural activity is external to and can not be directly modified; hence it can be considered part of the environment. The BMI agent 110 uses information in the neural signal to create movement commands (control actions) for a robot (or prosthetic limb), and strives to learn the optimal neural state 125 to control action 115 mapping.

Figure 2:
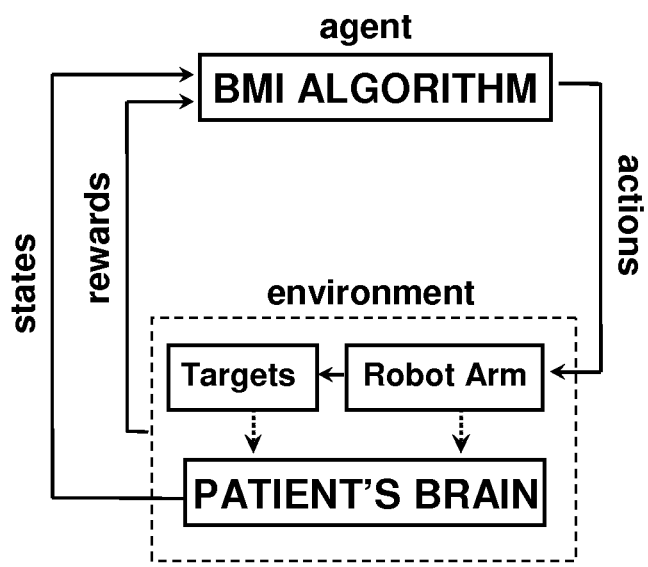
FIG. 2 depicts another exemplary embodiment of the BMI system of FIG. 1.

FIG. 2 illustrates a novel BMI architecture where the animal's (e.g. rat) neural signal is part of the environment. More specifically, the BMI system implementing the architecture defines the state, control actions occur in a discrete physical space (a separate portion of the environment), and the RLBMI algorithm serves as the 'agent'. In closed-loop testing, the animal can see the control actions of the robot; however, control actions do not directly influence the state of their brain. This is a fundamental shift in RL architecture because states are decoupled from control actions. In this paradigm, the robot position is not included in the state variable because this information reduces the problem to a basic 'grid-world' where neural signal would be ignored. However, the state may be augmented with other variables (e.g. prosthetic limb feedback); an appropriately designed augmented state may enhance RLBMI performance.

RL also assumes that the state variable is a Markov representation; therefore, instantaneous neural data must be embedded in time to satisfy the Markov assumption. RL is known to suffer from the 'curse of dimensionality' and the number of possible firing rate combinations is intractable in neural firing rate data. To define the 'neural state' of an animal (e.g. rat), binned estimates of neural firing rates were used from the forelimb area of primary motor cortex of a behaving animal. The neural firing rates can also be used to characterize the neural state of higher species (e.g. humans) for performing aspects of the embodiments of the invention herein. While there are other methodologies for quantifying neural activity, there is experimental and neurophysiological support for the theory that the brain utilizes rate coding. Additionally, there is evidence that the motor cortex provides a representation of the 'state' of the motor control environment that supports this approach. To define similar temporal sequences in neural states, the analysis system 112 first segments the animal's neural signals. For the animal (e.g. rat), the average trial-start to perform a task was approximately 1200 ms. Segments (1200 ms) of neural data were extracted from reward-earning trials. Each segment was defined relative to the animal's movement stop (pre-reward), the final 200 ms of the segments were excluded to account for nervous system to muscle conduction time. Trials shorter than 1200 ms were excluded. And equal left and right trials were required in the final dataset for balancing; the longest trials were excluded to balance the trial distribution.

The embodiments herein can model as a cooperative RL task the interaction of a paralyzed patient with an intelligent BMI prosthetic performing tasks in the environment both from the user's and the BMI's perspective. Users consider themselves the agent and act through the BMI to accomplish tasks (e.g. reach a glass of water) in the environment (e.g. the prosthetic, a glass of water). The user considers the positions of the prosthetic and the glass to be the environment's state. Since users can not move, their actions are a high level dialogue (neural modulations) with the BMI and the user may define reward as reaching the glass of water. The user seeks to learn a value for each action (neural modulation) given the relative position of the prosthetic (state) and the goal in order to achieve rewards.

The BMI controller defines the learning task differently. It considers itself the agent and acts through the prosthetic to accomplish tasks (e.g. reach the glass of water) in the environment (e.g. the user, the prosthetic). The BMI controller considers the environment's state to be the user's neuromodulation, where it is assumed that the user's spatio-temporal neuronal activations reflect his or her intentions based on perception of the prosthetic. The BMI controller must develop a model of its environment (through observation of neuromodulation) to successfully interpret user intent. The BMI control agent's actions are movements of the prosthetic and rewards are defined in the environment based on the user's goals. Although in the ultimate implementation of a neuroprosthetic, the goal states could be also translated from the subject intent, the first step is to demonstrate feasibility by providing the BMI agent rewards based on the prosthetic position in the 3-D environment. These rewards should coincide with the user's goal (i.e. assign rewards for reaching the glass). The BMI controller seeks to learn values for each action (prosthetic movement) given the user's neural modulations (state) in order to achieve rewards.

The RLBMI architecture creates an interesting scenario where there are two "intelligent systems" in the loop. Both systems are learning to achieve rewards based on their own interpretations of the environment. The RLBMI must both facilitate prosthetic control for the user and adapt to the learning of both systems such that they act symbiotically. FIGS. 1 and 2 show this RL framework for BMI. Although the user is also learning, embodiments herein focus on the design and testing of the BMI controller. Therefore, any future use of the term BMI agent refers to the BMI control algorithm.

The analysis system 112 incorporates data segmentation for demonstrative purposes. Other cues from the environment or patient can be used to develop a 'start-stop' signal, and segment the data without requiring patient movement. Further experimental testing has shown that the system does not require a balanced trial distribution—the RLBMI still had about 80% accuracy with a 25% difference in the trials per side. Additionally, using this RLBMI architecture in higher species (e.g. humans) may reduce the amount of data preprocessing that is currently necessary in rats.

Figure 3:
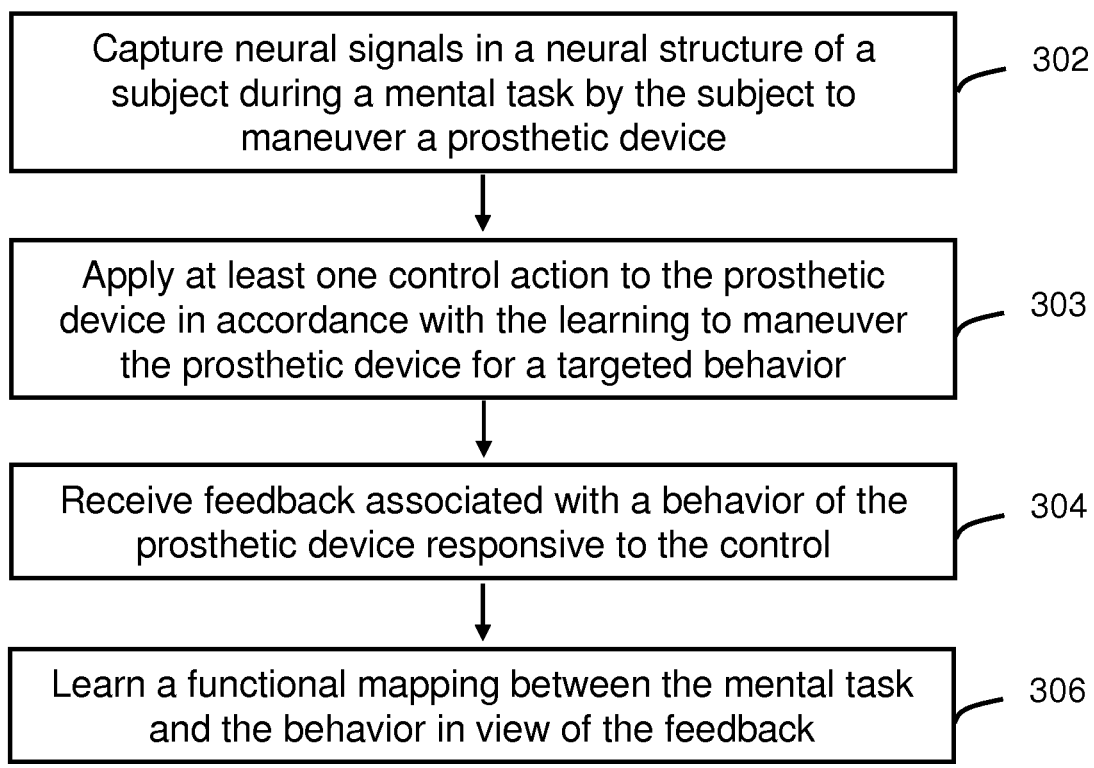
FIG. 3 depicts an exemplary method operating in the BMI system.

FIG. 3. presents an exemplary method for BMI control. The method 300 can include more or less than the number of steps shown, and is not limited to the order of the steps. The exemplary method can start in a state wherein a subject (e.g. animal) is fitted with a microelectrode implant connected to a BMI agent and a prosthetic device as shown in FIG. 2. At step 302, the microelectrode 120 captures neural signals in a neural structure of the subject during a mental task by the subject to control a prosthetic device 130. In one arrangement, the mental task can be a motor-movement related task to control an appendage, for example a non-paralyzed patient that has control of an appendage. In another case, the mental task can performed and captured even if the patient cannot physically move the appendage. For example, in the case of an amputee or paralyzed patient, the mental task is to contemplate moving the appendage though the appendage is missing. The microarray 120 can capture task related neural modulations even in the absence of movement. As another example, the patient may have a disabled appendage capable of receiving low-level sensory neural signals, though without full range of motion. The BMI agent 110 can map the range of mental control movement to a wider range of physical motion. At step 303, the BMI applies the control action 115 to the prosthetic device in accordance with the learning to control the prosthetic device for a targeted behavior. At step 304, the BMI agent 110 receives feedback associated with a behavior of the prosthetic device 130 responsive to the control, and identifies one or more states 125 in the neural signals. At step 306, the BMI agent 110 learns a functional mapping between the mental task corresponding to the states 125 and the behavior of the control actions 115 in view of the feedback.

Figure 4:
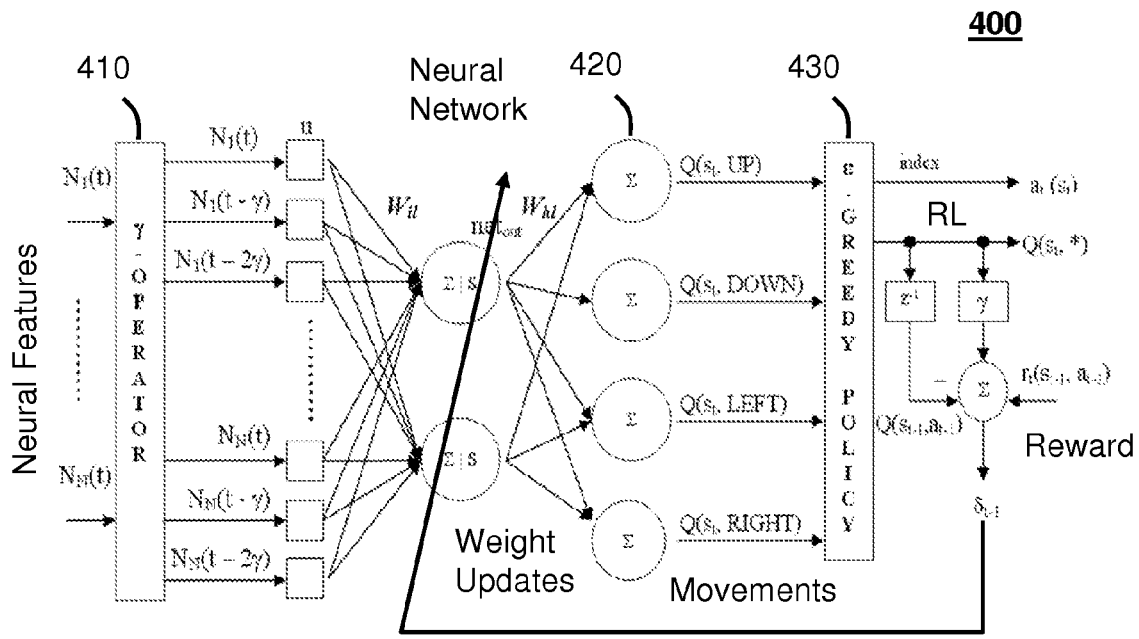
FIG. 4 depicts an exemplary neural network and additional components used for a reinforcement learning BMI (RLBMI)

FIG. 4, shows a neural network 400 of the analysis system which can generate a functional mapping between the states 125 and the control action 115 of the prosthetic device using reinforcement learning (RL). More specifically, the neural network incorporates RL to learn an association between the states 125 and the control action 115. The BMI agent 110 co-adapts with the subject's learning experience in controlling the prosthetic. The term co-adaptation referrers to two systems learning; the computational agent (e.g. neural network, Bayesian net) 400 and the subject (e.g. rat, patient).

The neural network 400 can include a Gamma structure front-end 410 with arbitrary time varying Gamma weight kernels receiving as input neural signals, a set of processing elements interconnected by weights in a lattice structure 420, and an $\epsilon$-greedy policy back-end 430 to evaluate exploratory control actions of the prosthetic device that produce a targeted behavior. The neural network 400 can learn from sequences of state-control action pairs using Watkins $Q(\lambda)$ reinforcement learning (RL). Watkins $Q(\lambda)$ learning is an off-policy learning method that can follow an $\epsilon$-greedy (sometimes exploratory) policy yet learn a greedy policy. The neural network 400 also assesses the rewards for updating the weights in the lattice 420. As an example, the gamma structure (K=2, $\lambda$=0.3) was used to preserve about 665 ms of firing rate history. The neural network 400 combines the gamma memory with a multi layer perceptron (MLP) to provide spatio-temporal segmentation. As an example, the neural network 400 can contain H nonlinearities and linear output processing elements (PE) associated with control actions (e.g. up, down, left, right movement). The neural network can implement various weight update techniques such as those that use a minimum square error criterion with back-propagation to update the weights during learning.

Figure 5:
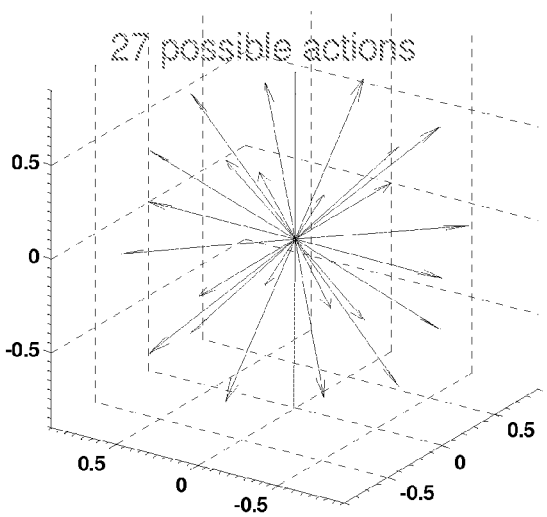
FIG. 5 depicts an exemplary set of control actions for a prosthetic device.
Figure 6:
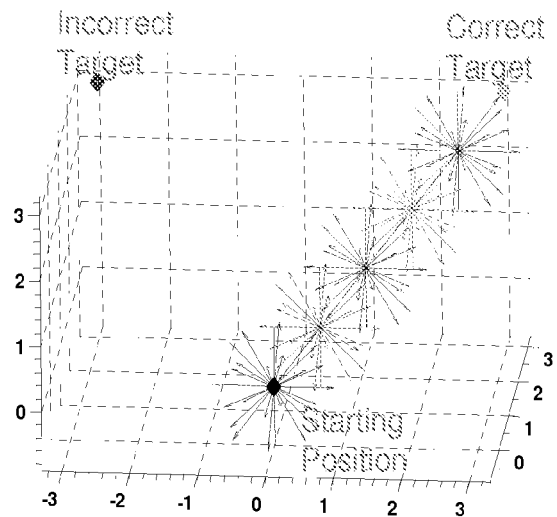
FIG. 6 depicts an exemplary movement trajectory for a prosthetic device (with possible control actions shown at each step)

Referring to FIG. 5, an exemplary set of possible control actions for the robot (e.g. prosthetic limb) are shown. FIG. 6 illustrates a movement trajectory of the robot along one or more points in a three-dimensional space. A reward is generated when a positioning of the robot (e.g. prosthetic limb) corresponds to a targeted behavior (e.g. intended positioning along a point of the trajectory). The environment (e.g. three-dimensional space) of the robotic movement is divided into discrete grid nodes. In the illustration, there are 27 possible control actions in the three-dimensional space: 1 unit in any single direction, 0.7 units in any direction pairs (diagonal moves), and 0.6 units in any direction triples (see FIG. 3). The scales for multi-dimension moves are necessary to restrict all control action vectors to the same length. In two (three) dimensions, a one-unit long vector at 45° to the axes, projects 0.7071 (0.5774) units on each axis. Notably, the number of control actions and the magnitude and direction of the control actions are application dependent and can include more or less than those shown. When the robot reaches a target location a positive reward is generated, the trial ends, and the robot is reset to the initial position. Each control action prior to reaching a lever generates a negative reward to encourage minimizing trial length.

Referring back to FIG. 4, the neural network or other adaptive system 400 can be trained on-line or offline with temporal-difference error and eligibility traces via back-propagation. The initial weights can be set to small, random values. The estimated neural firing rate history is the input (state 125) to the network (e.g. neural signals) wherein each output PE represents the value of one control action 115 (e.g. prosthetic device movement). In the exemplary embodiment, 46 segments (trials) of the neural data are used to train the neural networks, 16 segments are reserved for testing. The neural network 400 can learn from sequences of state-control action pairs (e.g. state 125 and control action 115) using Watkins Q(λ) reinforcement learning (RL). However, the RLBMI can incorporate more sophisticated RL algorithms. Q(λ) learning is an off-policy RL method that learns from sequences of state-control action pairs (See eqn. 1 below for the parameter update equation). See "Reinforcement Learning: an introduction" by R. S. Sutton and A. G. Barto, 1998 for further background information.

$$dQ(s_{t-1},a)=\alpha[r_t+\gamma Q(s_t,a^*_t)-Q(s_{t-1},a_{t-1})]e(s_{t-1},a) \qquad [1]$$

Q is the estimated state-control action value, dQ is the weight change in the network approximating Q, s is the state 125, e is the control action 115, α is the learning rate, γ is the discounting factor, e is the eligibility trace, and λ is the trace-decay parameter. The algorithm follows an ε-greedy policy. The value function is updated online; if RL parameters are appropriate, Q(λ) converges to the optimal policy.

Figures 7, 8:
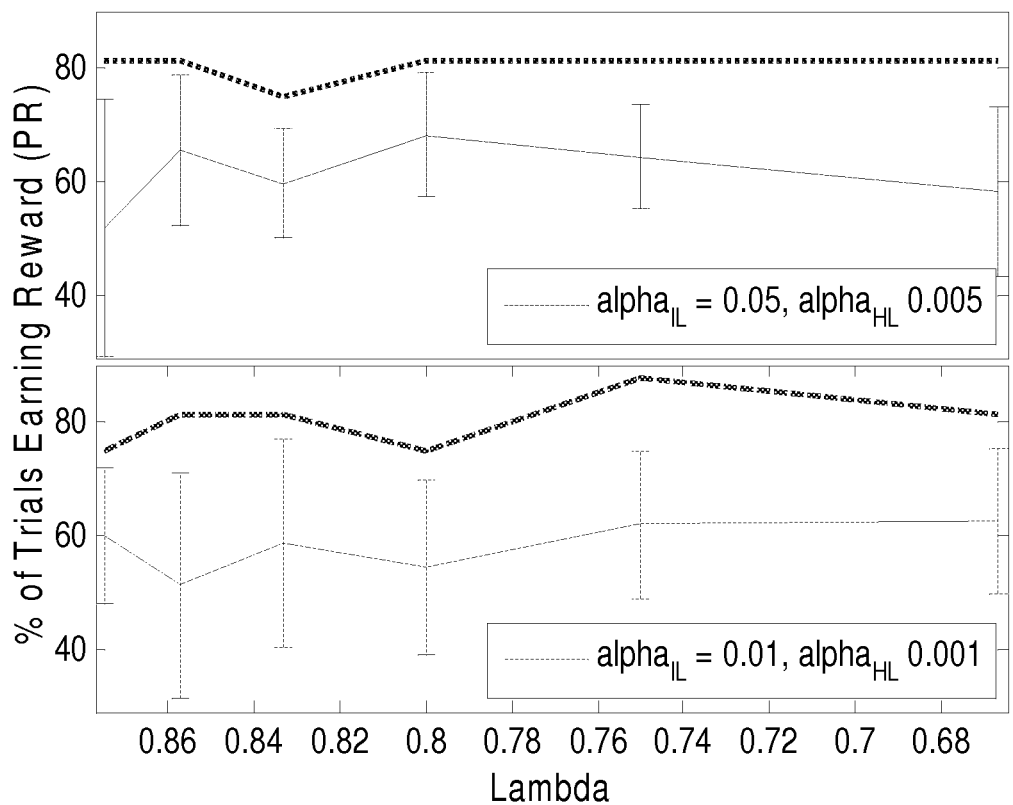
FIG. 7 depicts experimental results of the BMI system of FIG. 1.
FIG. 8 depicts the BMI system's robustness to user defined parameters.

FIG. 7 presents experimental results of the preliminary performance of the RLBMI system using rat neural data. FIG. 7 illustrates that the RLBMI can achieve goal directed movements of prosthetic limbs greater than 80% of the time for the conducted rat experiments. Test set performance of the RLBMI for two and three dimension grid environments are also shown in FIG. 7. FIG. 7 also shows the null hypothesis: that RL can learn from random state presentations and solve the task. The spatial and temporal relationships in the neural data are randomized to create a surrogate data set to test this null hypothesis. The surrogate data was tested with the best neural data parameter set.

The null hypothesis is disproved by the performance of the surrogate data. RLBMI can memorize the surrogate training data, but does not generalize to novel data. This suggests that RLBMI exploits movement-related information present in the spatio-temporal activation of the neural signal. RLBMI does generate a sequence of control actions, creating a trajectory in the prosthetic limb space. Although it may be desirable, there is no requirement that this artificial trajectory should match the kinematics of a natural limb. The path of the prosthetic limb is arbitrarily designated based on the reward distribution and must only match the timing of the natural limb trajectory. RLBMI potentially can learn a new trajectory for each neural modulation pattern.

FIG. 8 shows the BMI system's robustness to user defined parameters. In particular the plot shows that PR is fairly robust to λ and α selection, though all of the possible RLBMI parameter set combinations were not experimentally evaluated.

Upon reviewing the aforementioned embodiments, it would be evident to an artisan with ordinary skill in the art that said embodiments can be modified, reduced, or enhanced without departing from the scope and spirit of the claims described below. There are numerous configurations for other media services that can be conceived for configuring media resources in a media network that can be applied to the present disclosure without departing from the scope of the claims defined below. For example. The BMI system can be implemented by a computer or within a prosthetic limb for rehabilitation of humans with movement disabilities. As another example, the neural signals can be captured from other recording methods including Electrocorticography (ECoG), Electroencephalgoraphy (EEG), or any other neurophysiological or electro-based data acquisition technique. Additionally, the architecture can be incorporated into other BMI control schemes, and can serve as a switching mechanism on a mixture-of-experts system for choosing appropriate control 'experts'. The RLBMI generates a sequence of control actions, creating a trajectory for a computer or prosthetic limb. Although it may be desirable, there is no requirement that this artificial trajectory should match the kinematics of a natural limb and therefore can greatly expand the repertoire of available control schemes for a wide variety of applications. The path of the prosthetic limb is arbitrarily designated based on the reward distribution and must only match the timing of patient's neural modulation. These are but a few examples of modifications that can be applied to the present disclosure without departing from the scope of the claims stated below. Accordingly, the reader is directed to the claims section for a fuller understanding of the breadth and scope of the present disclosure.

Detailed embodiments of the present method and system have been disclosed herein. However, it is to be understood that the disclosed embodiments are merely exemplary, and that the invention can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiment herein.

Where applicable, the present embodiments of the invention can be realized in hardware, software or a combination of hardware and software. Any kind of computer system or other apparatus adapted for carrying out the methods described herein are suitable. A typical combination of hardware and software can be a mobile communications device with a computer program that, when being loaded and executed, can control the mobile communications device such that it carries out the methods described herein. Portions of the present method and system may also be embedded in a computer program product, which comprises all the features enabling the implementation of the methods described herein and which when loaded in a computer system, is able to carry out these methods.

The term "processing" can be defined as number of suitable processors, controllers, units, or the like that carry out a pre-programmed or programmed set of instructions. The terms "program," "software application," and the like as used herein, are defined as a sequence of instructions designed for execution on a computer system. A program, computer program, or software application may include a subroutine, a function, a procedure, an object method, an object implementation, an executable application, a source code, an object code, a shared library/dynamic load library and/or other sequence of instructions designed for execution on a computer system.

For example, the above-discussed embodiments may be implemented using software modules which perform certain tasks. The software modules discussed herein may include script, batch, or other executable files. The software modules may be stored on a machine-readable or computer-readable storage medium such as a disk drive. Storage devices used for storing software modules in accordance with an embodiment of the invention may be magnetic floppy disks, hard disks, or optical discs such as CD-ROMs or CD-Rs, for example. A storage device used for storing firmware or hardware modules in accordance with an embodiment of the invention may also include a semiconductor-based memory, which may be permanently, removably or remotely coupled to a microprocessor/memory system. Thus, the modules may be stored within a computer system memory to configure the computer system to perform the functions of the module. Other new and various types of computer-readable storage media may be used to store the modules discussed herein.

While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

What is claimed is:

1. A Brain Machine Interface (BMI) agent that, when operatively coupled to a subject during a mental task to control a prosthetic device, is configured to:
    monitor neural activity of the subject;
    determine a state of neural activity based upon monitored spatio-temporal neural activity associated with the mental task via an analysis system configured to determine the state of neural activity corresponding to the spatio-temporal neural activity, the analysis system comprising an adaptive system including a time embedding front-end with arbitrary time varying delay;
    apply a control action to the prosthetic device in response to the determined state of neural activity;
    receive reward feedback corresponding to a behavior of the prosthetic device that is in response to the control action; and
    learn a functional mapping between the state of neural activity and a state-action value of the control action in view of the reward feedback.

2. The BMI agent of claim 1, wherein the BMI agent is configured to co-adapt to learn, concurrently and continuously with learning by the subject, a value function between the state of neural activity and the state-action value based at least in part upon a positive or negative reward signal that is received by the BMI agent as reward feedback from an environment including the prosthetic device and a brain of the subject, where the subject receives a related reward from the environment.

3. The BMI agent of claim 1, comprising:
    a detection system configured to detect and collect neurophysiological signals corresponding to the spatio-temporal neural activity, the neurophysiological signals comprising action potentials of single or ensembles of neurons in a neural structure;
    the analysis system configured to assess one or more rewards corresponding to the behavior of the prosthetic device; and
    a controller configured to apply the at least one control action to the prosthetic device to adjust the behavior of the prosthetic device in accordance with the functional mapping.

4. The BMI agent of claim 3, wherein the analysis system is configured to comprise:
    a neural network that generates a functional mapping between the state of neural activity and the state-action value of the control action using reinforcement learning (RL) to learn an association between the state of neural activity and the control action.

5. The BMI agent of claim 4, wherein the neural network uses the one or more rewards to update a learning of the functional mapping, wherein the one or more rewards includes at least one positive or negative reward signal provided in response to a controlled movement of the prosthetic device, and the state of neural activity corresponds to a spatio-temporal neural firing pattern.

6. The BMI agent of claim 1, wherein the adaptive system is a neural network that comprises a time embedding Gamma structure front-end with arbitrary time varying delay using Gamma weight kernels or any other time embedding structure.

7. The BMI agent of claim 1, wherein the adaptive system comprises an $\epsilon$-greedy policy back-end to evaluate exploratory control actions of the prosthetic device to produce a targeted behavior.

8. The BMI agent of claim 6, wherein the neural network learns from sequences of state-control action pairs using Watkins $Q(\lambda)$ reinforcement learning (RL).

9. The BMI agent of claim 3, wherein the detection system comprises:
    an array of a plurality of electrodes forming a multi-site array to monitor the neural activity; and
    a spike sorter to extract neural firing features from the neural activity and distinguish between neurons generating the neural activities.

10. The BMI agent of claim 3, wherein the analysis system is configured to:
    evaluate the detected and collected neurophysiological signals to determine the state of neural activity based upon neuron firing features;
    perform a real-time control action based upon the determined state of neural activity, and
    learn one or more state-action values of the control action for the determined state of neural activity based at least in part upon the one or more rewards.

11. The BMI agent of claim 1, wherein the at least one control action is a relative movement of a robotic appendage of the prosthetic device in a three-dimensional coordinate space, and a target behavior is a positioning of the robotic appendage along at least one point of a three-dimensional trajectory in the three-dimensional coordinate space.

12. A neural prosthetic system comprising:
    a micro-electrode array electro-chemically coupled to a neural structure of a subject to capture spatio-temporal neural activity in the neural structure;
    a controlled prosthetic device that performs one or more behaviors for the subject in accordance with the spatio-temporal neural activity; and
    a Brain Machine Interface (BMI) agent operatively coupled to the micro-electrode array and the controlled prosthetic device that is configured to:
    monitor the spatio-temporal neural activity to determine a corresponding state of neural activity,
    receive reward feedback corresponding to a behavior of the controlled prosthetic device where the behavior is in response to an applied control action,
    co-adapt, concurrently and continuously along with learning by the subject, to learn a functional mapping to a possible control action given the determined state of neural activity in view of the reward feedback, and
    apply the control action to the controlled prosthetic device in accordance with the learned functional mapping to maneuver the controlled prosthetic device for a targeted behavior;
    the BMI agent comprising an analysis system configured to determine the corresponding state of neural activity from neural firing rates of the spatio-temporal neural activity, where the analysis system is configured to comprise a state-action value estimator that comprises a neural network that generates the functional mapping between the state of neural activity and a state-action value of the control action using reinforcement learning (RL) to learn an association between the state of neural activity and the control action, where the neural network comprises:

a time embedding structure comprising a Gamma structure front-end with arbitrary time varying Gamma weight kernels; and
an $\epsilon$-greedy policy back-end to evaluate exploratory control actions of the prosthetic device to produce a targeted behavior,
wherein the neural network learns from sequences of state-control action pairs using Watkins Q($\lambda$) reinforcement learning (RL).

13. The neural prosthetic system of claim 12, wherein the BMI agent comprises:
a detection system communicatively coupled to the microelectrode array to determine the neural firing rates from the spatio-temporal neural activity, the analysis system communicatively coupled to the detection system; and
a controller to apply the control action to the controlled prosthetic device to adjust the behavior of the controlled prosthetic device in accordance with the functional mapping which provides the state-action value given the determined state of neural activity.

14. The neural prosthetic system of claim 13, wherein the controlled prosthetic device is a robotic appendage, and the BMI agent controls the robotic appendage in a three-dimensional coordinate space in accordance with the control action given the determined state of neural activity.

15. The neural prosthetic system of claim 14, wherein the targeted behavior comprises positioning of the robotic appendage along at least one point of a three-dimensional trajectory in the three-dimensional coordinate space by applying at least one control action selected based upon a corresponding state-action value.

16. The neural prosthetic system of claim 12, wherein the neural structure is selected from the group consisting of the motor-cortex, limbic system, sensory cortex, parietal cortex, cerebellum, red nuclei, basil ganglia, hippocampus, entorhinal cortex, CA1, CA2, CA3, dentate, and hippocampal commissure.

17. The neural prosthetic system of claim 12, wherein the BMI agent is implemented by a Digital Signal Processor or an Application Specific Integrated Circuit (ASIC).

18. A method for Brain Machine Interface (BMI) control, the method comprising:
capturing spatio-temporal neural signals in a neural structure of a subject during a mental task by the subject to control a prosthetic device through an applied control action;
determining, by an analysis system of a BMI agent, a state of neural activity based upon the captured spatio-temporal neural signals, where the analysis system comprises an adaptive system including a time embedding front-end with arbitrary time varying delay;
receiving, by the BMI agent, reward feedback corresponding to a behavior of the prosthetic device that is in response to the applied control action;
learning, by the analysis system of the BMI agent, a functional mapping between the state of neural activity and a state-action value of the applied control action based at least in part upon the reward feedback; and
applying another control action to the prosthetic device in accordance with the learned functional mapping to control the prosthetic device for a targeted behavior.

19. The method of claim 18, wherein a state-action value estimator receives as input the spatio-temporal neural signals and one or more rewards corresponding to the behavior of the prosthetic device, and adapts one or more weights of a neural network using reinforcement learning (RL) to learn the functional mapping between the state of neural activity and the state-action value based at least in part upon the one or more rewards.

20. The method of claim 19, further comprising pre-processing the neural signals with a non-linear gamma time-delay kernel prior to input to the state-action value estimator.

21. The method of claim 19, further comprising implementing an $\epsilon$-greedy policy back-end configured to select control actions applied to the prosthetic device that produce a targeted behavior.

22. The method of claim 19, wherein a plurality of control actions are selected based upon the state-action value of the neural network to control an endpoint position of a robotic appendage of the prosthetic device operating in a three-dimensional space to reach a set of targets.

23. The method of claim 22, wherein the one or more rewards are associated with one or more identified positions of the robotic appendage in the three-dimensional space, and a positive reward is generated when the robotic appendage reaches a target location.

24. The method of claim 19, wherein the neural network is trained using RL with inputs corresponding to the state of neural activity, the control action applied to the prosthetic device, and the one or more rewards corresponding to the behavior of the prosthetic device, wherein the neural network is trained online during prosthetic control without a prior training set.

25. The method of claim 24, wherein the neural network learns from sequences of state-control action pairs that generate movement trajectories of the prosthetic device.

26. The method of claim 18, wherein the neural signals are captured via Electrocorticography (ECoG) or Electroencephalography (EEG).

27. The method of claim 18, wherein a neural network learns the functional mapping from sequences of state-control action pairs using Watkins Q($\lambda$) reinforcement learning (RL), the neural network comprising a time embedding structure comprising a Gamma structure front-end with arbitrary time varying Gamma weight kernels.

28. The method of claim 27, wherein the neural network further comprises an $\epsilon$-greedy policy or other policy back-end to evaluate exploratory control actions of the prosthetic device that produce a targeted behavior.

* * * * *